United States Patent [19]

Di Martino et al.

[11] Patent Number: 5,393,492
[45] Date of Patent: Feb. 28, 1995

[54] MICROWAVE CHEMICAL REACTOR FOR SAMPLE ANALYSIS

[75] Inventors: Jean-Louis Di Martino, Briare; Patrick Jacquault, Sevres; Jean-Louis Millet, Thiais; Jacques Paturat, Briare, all of France

[73] Assignee: Societe Prolabo, Paris Cedex, France

[21] Appl. No.: 169,540

[22] Filed: Dec. 20, 1993

Related U.S. Application Data

[63] Continuation of Ser. No. 735,314, Jul. 24, 1991, abandoned.

[30] Foreign Application Priority Data

Jul. 24, 1990 [FR] France ................... 90 09663

[51] Int. Cl.⁶ ............... G01N 22/00; B01J 19/12
[52] U.S. Cl. ........................ 422/62; 422/63; 422/81; 422/132; 422/138; 436/52; 436/174; 436/179; 436/180; 417/521
[58] Field of Search ........... 422/62, 81, 138, 132, 422/63; 436/52, 53, 174, 175, 179, 180; 417/521, 505

[56] References Cited

U.S. PATENT DOCUMENTS

| | | |
|---|---|---|
| 828,412 | 8/1906 | Larson ................. 417/521 |
| 2,730,952 | 1/1956 | Whiffen ................ 417/521 |
| 3,449,082 | 6/1969 | Baumann et al. ........... 23/253 |
| 3,535,482 | 10/1970 | Kluck ............... 219/10.55 R |
| 3,700,335 | 10/1972 | Seelbinder ............ 436/52 X |
| 3,883,309 | 5/1975 | Ishizawa et al. ........... 422/138 |
| 4,013,413 | 3/1977 | Stewart et al. ........... 436/52 X |
| 4,683,211 | 7/1987 | Onizuka et al. ........... 436/50 |
| 4,794,806 | 1/1989 | Nicoli et al. ........... 73/863.01 |
| 4,795,713 | 3/1989 | Koop et al. ............ 436/175 |
| 4,946,797 | 8/1990 | Neas et al. ............ 436/175 |
| 4,978,506 | 12/1990 | Calderwood ............ 422/73 |
| 5,066,199 | 11/1991 | Reese et al. ............ 417/63 |

FOREIGN PATENT DOCUMENTS

| | | |
|---|---|---|
| 0156742 | 10/1985 | European Pat. Off. . |
| 0275826 | 7/1988 | European Pat. Off. . |
| 2281159 | 3/1976 | France . |
| 9003840 | 4/1990 | WIPO . |

*Primary Examiner*—James C. Housel
*Assistant Examiner*—Long V. Le
*Attorney, Agent, or Firm*—Burns, Doane, Swecker & Mathis

[57] ABSTRACT

A chemical reaction is carried out by the wet method on a succession of samples. The chemical reaction is carried out within a reaction chamber which is connected to a fluid-conducting circuit. The reaction chamber is positioned within a microwave cavity. A predetermined quantity of sample is fed into the circuit upstream of the reaction chamber. At least one reactant is introduced into the circuit upstream of the reaction chamber. The reaction chamber, with the sample and reactant disposed therein, is heated by the application of microwaves for a predetermined time. The product of the reaction is recovered. The circuit is then rinsed with a rinsing liquid, and the steps are repeated on the remaining samples.

4 Claims, 4 Drawing Sheets

MICROWAVE CHEMICAL REACTOR FOR SAMPLE ANALYSIS

This application is a continuation of application Ser. No. 07/735,314, filed Jul. 24,1991, now abandoned.

BACKGROUND OF THE INVENTION

1. Field of the Invention

The present invention relates to a process for carrying out a chemical reaction by the wet method on a succession of samples, the process employing microwave heating of the sample into which at least one reactant has been introduced. It also relates to an apparatus for carrying out a chemical reaction by the wet method on a succession of samples, which employs the process which is the subject of the invention. The use of the apparatus, for example for the mineralization of samples, also forms part of the invention.

2. Description of the Prior Art

An apparatus and process for carrying out a chemical reaction by the wet method on a series of samples are known, wherein the samples are prepared beforehand and introduced into flasks placed in the housing of a carousel. The flasks are then conveyed to the microwave application cavity of a microwave generator (see for example European Patent No. 156,742). This apparatus, which is marketed by the company PROLABO under the designation MICRODIGEST 300, is well suited to the general requirements, but is difficult to adapt to receive samples directly from a sampling line or to couple it directly to an apparatus for continuous analysis. Such an apparatus and process are used for carrying out a wide variety of chemical reactions, such as the acid or alkaline treatment of samples by the wet method for purposes of dissolution, hydrolysis, or mineralization.

There is sometimes a need to be able to carry out chemical reactions by the wet method on samples coming directly from sampling lines.

SUMMARY OF THE INVENTION

Accordingly, a major object of the present invention is the provision of an improved process and apparatus for carrying out a chemical reaction by the wet method. The apparatus should be able to interconnect a sampling line, and either a collector for the products of the chemical reactions or an analyzer for the various products of the chemical reactions.

The expression "a succession of samples" is not intended to denote a set of individual samples prepared beforehand before being placed in the situation of undergoing a chemical reaction, but rather is intended to denote samples withdrawn, at regular intervals or otherwise, from a sampling line and introduced directly into the apparatus, that is to say without prior preparation apart from predetermination of the quantity of samples to be treated. The predetermined quantity of samples is defined either by its volume or by its mass.

Briefly, the presently claimed invention features carrying out a chemical reaction by the wet method on a succession of samples. A circuit is provided to which a reaction chamber is connected, the latter being physically positioned in a microwave cavity. A predetermined quantity of sample is fed into the circuit upstream of the reaction chamber. At least one reactant is introduced into the circuit upstream of the reaction chamber. The reaction chamber is heated, with the sample and reactant disposed therein, by the application of microwaves for a predetermined time. The product of the reaction is recovered. Eventually, the circuit is rinsed with a rinsing liquid, and the steps are repeated on each of the remaining samples.

BRIEF DESCRIPTION OF THE DRAWINGS

The objects and advantages of the invention will become apparent from the following detailed description of the preferred embodiment thereof in connection with the accompanying drawings, in which like numerals designate like elements, and in which.

DETAILED DESCRIPTION OF THE PREFERRED EMBODIMENTS OF THE INVENTION

More particularly, according to the present invention, a circuit contains a reaction chamber located in a microwave application cavity, and thereafter:

a) a predetermined quantity of sample is fed upstream of the reaction chamber, b) at least one reactant is introduced upstream of the reaction chamber, c) the reaction chamber is heated by application of microwaves for a predetermined time, d) the product of the reaction is recovered, e) a rinsing liquid is fed at the point of entry of the circuit, and the circuit is rinsed, f) the operations a) to e) are repeated as many times as necessary to effect the desired reaction.

In some cases, it may be desirable to carry out a chemical reaction by the wet method on a known product, e.g., for calibration purposes. For this purpose, the operations a) to e) above are performed replacing the sample by the known product, which shall be referred to as a "standard".

The operations a) to e) may naturally be performed several times with various standards.

According to an embodiment of the process, after the reaction mixture comprising the sample and the reactant (or reactants) has been heated, the product of the reaction may be cooled.

Figure 3:
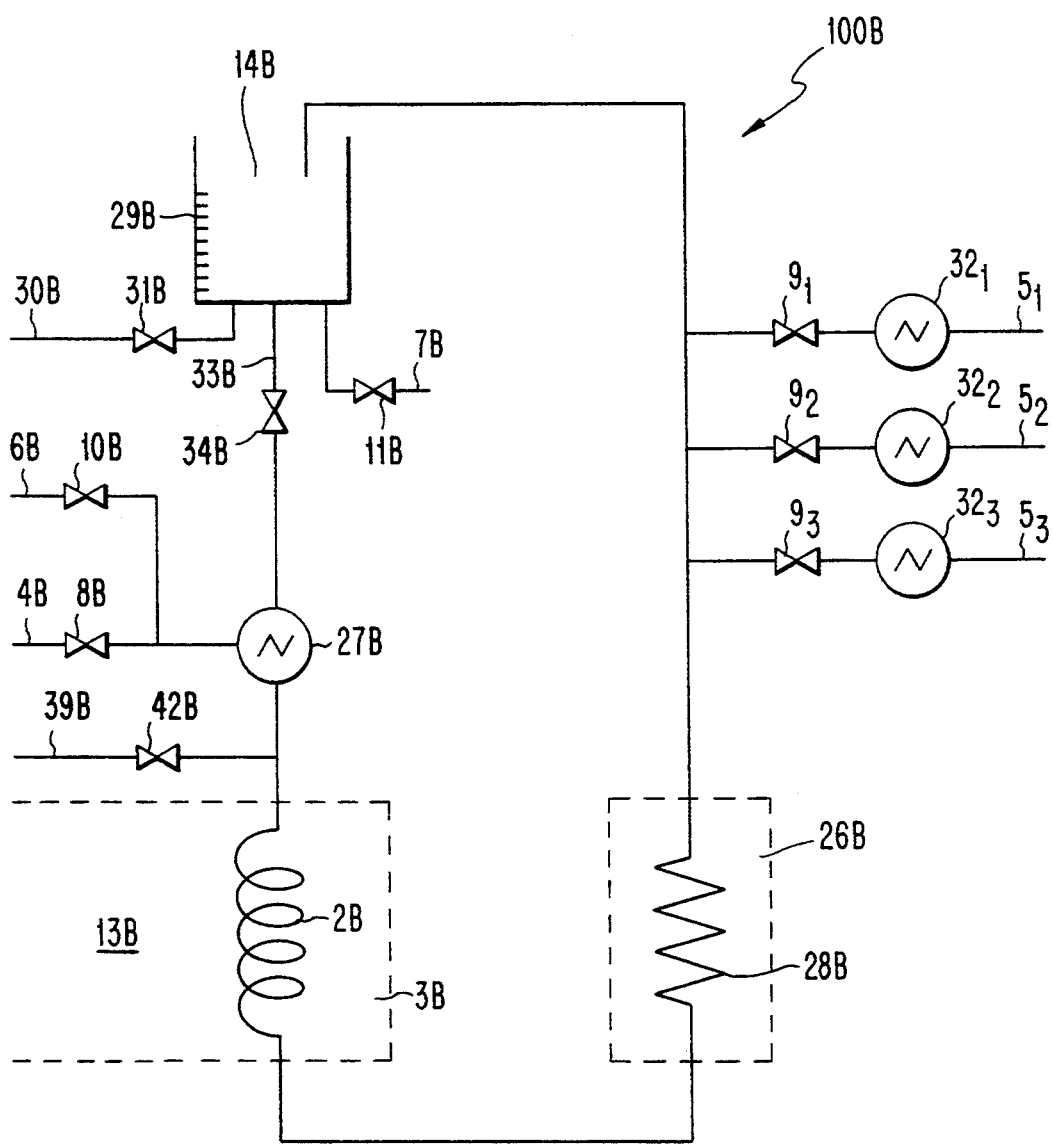
FIG. 3 shows diagrammatically a third embodiment of the apparatus which contains a looped circuit.
Figure 4:
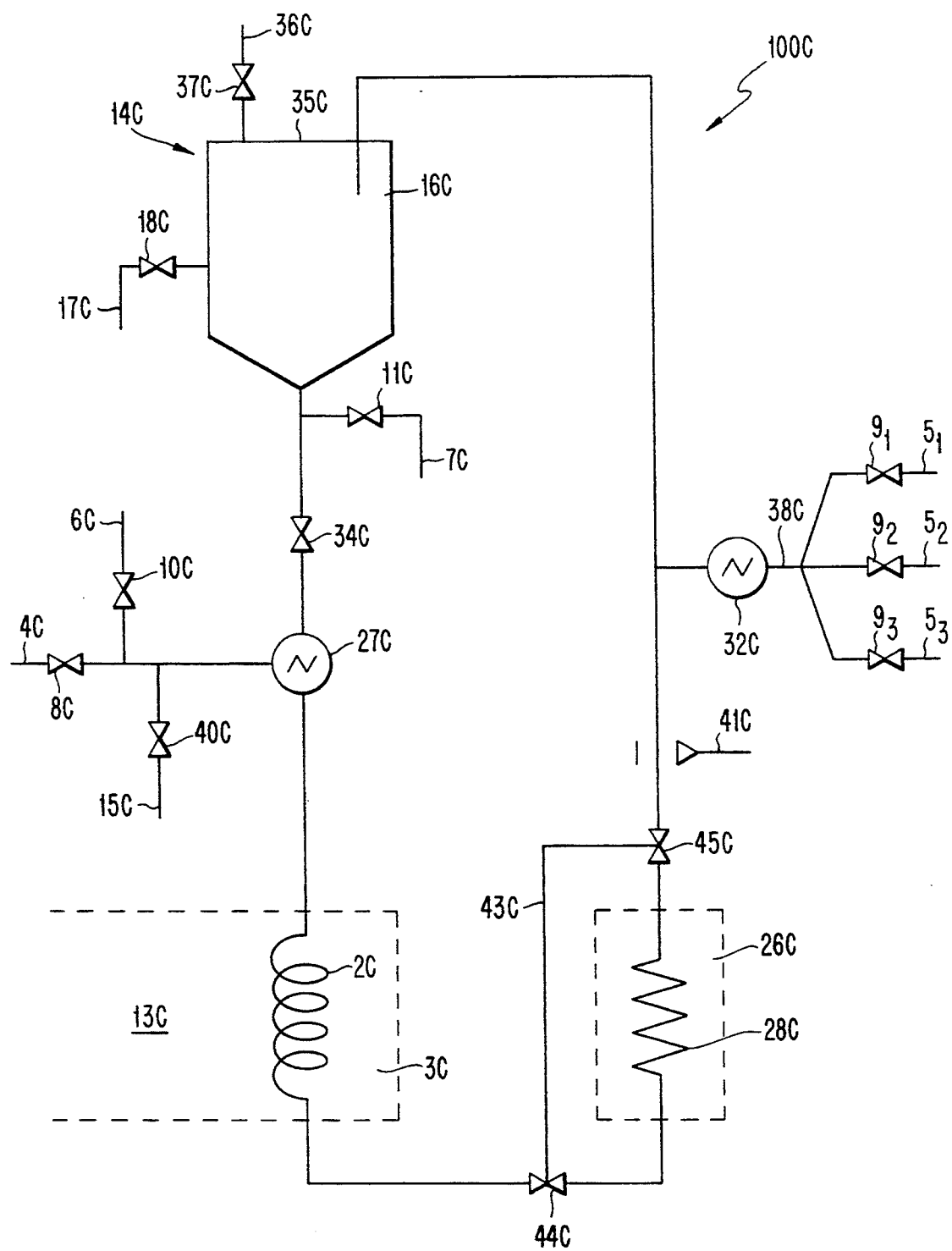
FIG. 4 shows diagrammatically a fourth embodiment of the apparatus which contains a looped circuit.

According to other preferred embodiments disclosed in connection with FIGS. 3 and 4, the circuit is a looped circuit containing circulation means, wherein:

a) a predetermined quantity of sample is fed into the looped circuit, b) the sample is circulated in the looped circuit, c) at least one reactant is introduced into the looped circuit, d) the reaction chamber is heated by application of microwaves for a predetermined time, e) the product of the reaction is recovered, f) the rinsing liquid is fed in and the looped circuit is rinsed, g) the operations a) to f) are repeated as many times as necessary.

Generally, several reactants are introduced into the looped circuit; these reactants may be introduced at the same point. Preferably, the reactants are introduced at several time points; after each introduction of reactant, the reaction chamber is heated by microwaves for a predetermined time. Advantageously, the reactants are introduced individually into the looped circuit; thus, between the operations b) and e) described above, the operations c) and d) are repeated for each reactant.

According to an embodiment of the process, the operations a) to f) can, as above, be repeated replacing the sample by a standard. The operations a) to f) may naturally be performed successively with different standards.

According to another embodiment of the process which is the subject of the invention, the product of the reaction may be cooled after each operation d).

Advantageously, as the chemical reaction proceeds, the progress of the reaction is monitored by monitoring means placed downstream of the reaction chamber.

To carry out the process described above, there has also been found, and this is another feature of the invention, an apparatus for carrying out a chemical reaction by the wet method on a succession of samples, characterized in that it comprises a circuit containing a reaction chamber placed in a microwave application cavity. Disposed upstream of the reaction chamber (considered with reference to the direction of travel of the sample in the circuit) there is disposed a sample feed pipe, at least one pipe for introduction of a reactant, and a rinsing liquid feed pipe. Each pipe is equipped with a valve. Downstream of the reaction chamber, there is provided an outflow pipe for the product of the reaction.

The microwaves are produced by a microwave generator of any known type, which is combined with an application cavity in which the reaction chamber is placed.

As a microwave application cavity, those marketed by the company PROLABO under the name MICRODIGEST 300 and MAXIDGEST MX 350 may be used.

The shape of the reaction chamber is not critical; a tubular reaction chamber is especially suitable.

It has been recited above that, considered with reference to the direction of travel of the sample in the circuit, a sample feed pipe, at least one pipe for introduction of a reactant and a rinsing liquid feed pipe are to be found upstream of the reaction chamber. It should be understood that the order of listing of the various pipes implies no assumptions as to their respective positions; it means only that the sample, the reactant and the rinsing liquid are introduced into the circuit upstream of the reaction chamber.

These pipes, each equipped with a valve, can open individually into the circuit; they can also be in parallel and linked to a common pipe which connects with the circuit.

The apparatus can contain a single pipe for introduction of a reactant; it can naturally contain several pipes for introduction of several reactants; these pipes can open individually into the circuit; they can also be in parallel and linked to a common pipe which connects with the circuit.

The rinsing liquid can be, for example, the liquid used for carrying out the chemical reaction; it can also be water.

According to an embodiment, the apparatus which is the subject of the invention can contain, upstream of the reaction chamber, a pipe for feeding a standard, optionally equipped with a valve. This pipe can join the sample feed pipe downstream of its valve.

According to the process for carrying out a chemical reaction by the wet method according to the invention, a predetermined quantity of sample is fed into the circuit. The sampling line can thus contain means for determining a volume or a mass of sample to be treated.

Advantageously, the apparatus which is the subject of the invention is such that the circuit contains means of adjustment of the quantity of sample.

More often than not, the means of adjustment of the quantity of sample are means of adjustment of the volume of the sample.

According to an embodiment, the means of adjustment of the volume of the sample possess a receptacle combined with the sample feed pipe, the receptacle being equipped with an overflow outlet carrying a valve.

According to another embodiment, the means of adjustment of the volume of the sample possess a graduated receptacle combined with the sample feed pipe, the receptacle being equipped with a drainage pipe carrying a valve. According to this embodiment, different sample volumes may be fed into the circuit of an apparatus, and the choice and adjustment of the volume of the sample may be readily automated using level detector associated with the receptacle.

When the circuit contains a receptacle, the reactant or reactants may be introduced into the circuit directly in the receptacle; thus, mixing between the reactant or reactants and the sample may be effected, the pipe linking the receptacle to the remainder of the circuit being equipped with a valve.

The reactant or reactants may also be introduced into the circuit downstream of the receptacle. It is then advantageous that a mixing chamber be placed in the circuit downstream of the final pipe for admission of a reactant, directly at the point of entry of the reaction chamber, the pipe linking the mixing chamber and the reaction chamber being equipped with a valve. Thus, in the mixing chamber, mixing between the reactant or reactants and the sample may be effected.

According to yet another embodiment, the apparatus according to the invention can contain, at the point of outflow of the reaction chamber, a zone for cooling the production of the reaction.

In the apparatus, the sample (or standard), the reactant or reactants, the rinsing liquid, the product of the reaction can flow in the circuit under the effect of gravity or alternatively under the effect of the pressure of the sample, or of the reactant or reactants, or of the rinsing liquid. Preferably the apparatus is such that it contains circulation means which can consist of a pump of any type customarily used.

As a circulation means, a positive-displacement pump delivering a continuous flow is preferably used. Advantageously, such a pump contains at least two plungers mounted in opposition, shifted by a cam rotating about an axis perpendicular to the axis of travel of the plungers, and yieldably biased return means associated with each plunger.

Advantageously, the circuit is a looped circuit which contains an expansion vessel, the outflow pipe for the product of the reaction being equipped with a valve. Such a looped circuit enables the reaction chamber to be heated after each introduction of reactant. The expansion vessel permits the increase in volume of the liquid contained in the circuit, this increase being due to the introduction of the reactants into the circuit.

The expansion vessel can, according to an embodiment, be the receptacle of the means of adjustment of the volume of the sample.

In the looped circuit, any product, such as sample, reactant, standard or rinsing liquid, which, during implementation of the process, is to pass through the reaction chamber is said to be introduced into the looped circuit upstream of the reaction chamber. Thus, the product of the reaction leaves the circuit downstream of the reaction chamber since it no longer passes through the reaction chamber.

According to yet another embodiment, the apparatus can contain means for monitoring the progress of the reaction.

The means for monitoring the progress of the reaction can consist of a measuring probe placed in the product of the reaction, measuring, for example, the conductivity of the latter. The monitoring means can also operate by measuring the optical density or by monitoring the coloration of the product of the reaction, a zone of the circuit being made of transparent material.

The apparatus for chemical reaction by the wet method according to the invention may be controlled manually by an operator operating the different valves, the microwave heating and, where appropriate, the circulation means and/or the cooling zone according to a predetermined cycle.

Preferably, the apparatus contains control means, such as a microprocessor, which operate the opening and closing of the valves and the switching on and off of the microwave heating and, where appropriate, of the circulation means and/or of the cooling zone according to a predetermined cycle.

The apparatus for chemical reaction which is the subject of the invention is advantageously made of highly corrosion-resistant materials, the reactants used being especially corrosive and the temperature reached in the reaction chamber being high. Thus, such an apparatus is made of glass and/or polytetrafluoroethylene.

The apparatus for chemical reaction which is the subject of the invention can carry out various chemical reactions by the wet method on a succession of samples. It is especially intended for use for chemical reactions of mineralization of succession of samples.

Figure 1:
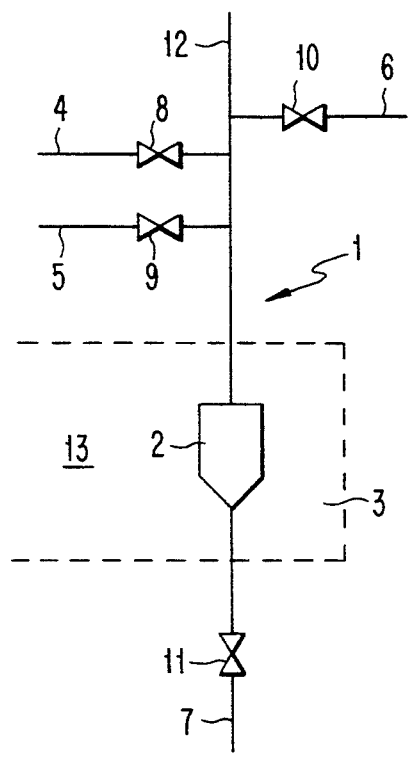
FIG. 1 shows diagrammatically a first embodiment of an apparatus for carrying out a chemical reaction by the wet method on a succession of samples, according to the invention.

An apparatus for carrying out a chemical reaction by the wet method on a succession of samples, employing microwave heating, shown in FIG. 1 comprises a circuit 1 containing a reaction chamber 2, the latter being physically located in a microwave application cavity 3 which comprises the terminal segment of a wave guide 13.

Considered with reference to the direction of travel of the sample in the circuit 1, the apparatus contains, upstream of the reaction chamber 2: a sample feed pipe 4, a reactant feed pipe 5 for introduction of at least one reactant, and a rinsing liquid feed pipe 6. Downstream of the reaction chamber 2, the apparatus has an outflow pipe 7 for conducting the product of the reaction.

The sample feed pipe 4, the reactant feed pipe 5, and the rinsing liquid feed pipe 6 are equipped with valves 8, 9, 10, respectively.

The reactant feed pipe 5 can introduce into the circuit 1 a single reactant or several reactants successively, or alternatively a mixture of at least two reactants, according to the requirements of the chemical reaction.

The outflow pipe 7 is also equipped with a valve 11 intended for preventing the product from flowing out of the circuit 1 during the time necessary for accomplishment of the reaction in the reaction chamber 2.

The circuit 1 of the apparatus also has a pipe referred to as a vent 12, intended for placing the internal space of the circuit 1 in communication with the atmosphere. The vent 12 makes it possible for gases evolved in the chemical reaction to escape from the circuit 1.

The functioning of the apparatus, on carrying out the process according to the invention, will be described briefly below.

The sample feed pipe 4 is linked to a source of samples comprising, for example, a sampling line coming from an installation. Similarly, the rinsing liquid feed pipe 6 is linked to a source of rinsing liquid.

Where the valves 8, 9, 10, 11 have been closed beforehand, the valve 8 of the sample feed pipe 4 is opened and a predetermined quantity of a sample is fed into the circuit 1 upstream of the reaction chamber 2, for example by means of a positive-displacement pump. The valve 8 is then closed again.

The valve 9 of the pipe 5 for introduction of reactant is opened and the desired quantity of reactant is introduced into the circuit 1 for example by means of a positive-displacement pump; the valve 9 is then closed again.

The sample and the reactant are hence present in the reaction chamber 2. The microwave generator is operated for a predetermined time, and the reaction chamber and contents thereof are thereby heated.

The valve 11 is then opened and the product of the chemical reaction is recovered via the outflow pipe 7, this product leaving the circuit 1 under the effect of gravity.

When all of the product of the reaction has been recovered, the valve 10 of the rinsing liquid feed pipe 6 is opened and the circuit is rinsed. The contaminated rinsing liquid leaves the circuit 1 via the pipe 7 and is directed to an effluent storage tank.

When the rinsing of the circuit 1 is complete, the valve 10 of the rinsing liquid feed pipe 6 and then the valve 11 of the outflow pipe 7 are closed; the apparatus is ready to receive a further sample fed via the pipe 4 and to carry out a chemical reaction by the wet method on a further sample, repeating the above-described operations.

Figure 2:
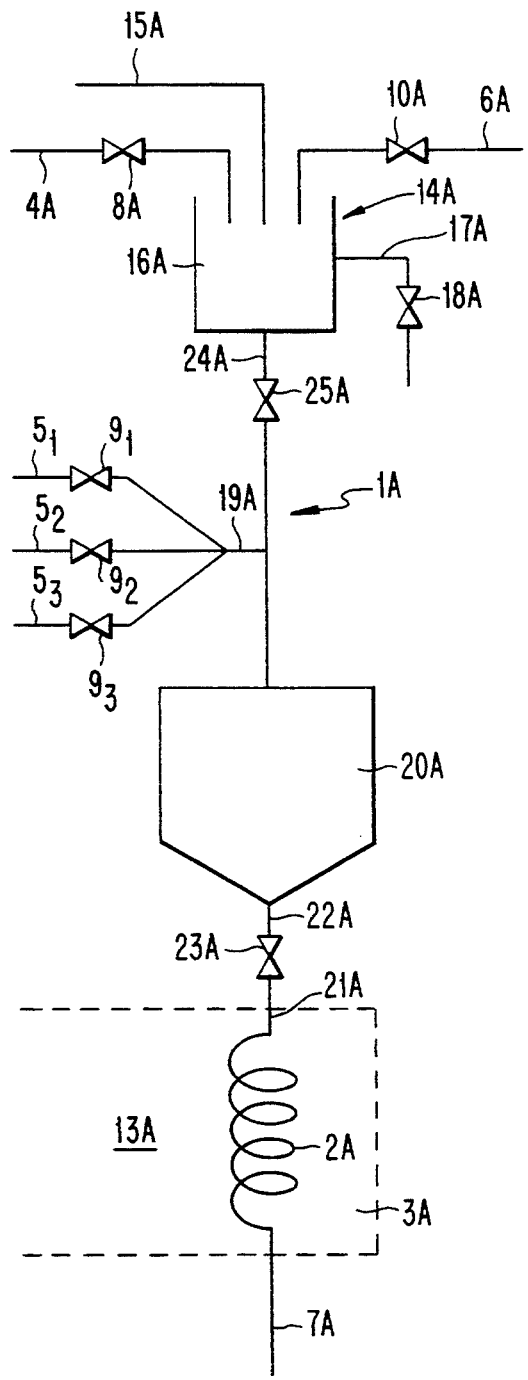
FIG. 2 shows diagrammatically a second embodiment of the apparatus.

The apparatus for carrying out a chemical reaction on a succession of samples according to the embodiment shown in FIG. 2 comprises a circuit 1A containing reaction chamber 2A placed in a microwave application cavity 3A. It comprises, in addition, an adjustment device 14A for adjusting the quantity of sample, and a pipe 15A for feeding a calibrating standard.

The adjustment device 14A functions to adjust the volume of the sample. According to the present embodiment, it comprises an expansion vessel in the form of a receptacle 16A into which the sample feed pipe 4A opens, the receptacle 16A being equipped with an overflow outlet 17A carrying a valve 18A and with a pipe 24A for linkage to the remainder of the circuit 1A, provided with a valve 25A.

The pipe 15A and the rinsing liquid feed pipe 6A, equipped with a valve 10A, also open into the receptacle 16A.

The receptacle 16A is open in order to enable gases to escape from the chemical reaction.

The circuit 1A as shown contains three pipes $5_1$, $5_2$, $5_3$ for the introduction of reactants, the pipes being equipped with valves $9_1$, $9_2$, $9_3$, respectively; these three pipes are mounted in parallel and are linked to a common pipe 19A which connects with the circuit 1A.

Downstream of the common pipe 19A for the introduction of the reactants into the circuit 1A, the latter has a mixing chamber 20A placed directly at the point of entry 21A of the reaction chamber 2A. The pipe 22A linking the mixing chamber 20A, and the reaction chamber 2A is equipped with a valve 23A.

The reaction chamber 2A as shown is tubular and coiled in a spiral; its geometrical features have been determined so that the residence time of the sample and of the reactants is sufficient to achieve the desired reaction in the reaction chamber 2A. The product of the reaction flows out directly via the outflow pipe 7A.

The carrying out of a chemical reaction by means of the apparatus according to the present embodiment will be described briefly below.

With the standard feed pipe 15 connected to a source of standard; with the sample feed pipe 4A and the rinsing liquid feed pipe 6A linked, respectively, to a source of samples and to a source of rinsing liquid, the valves 8A, 10A, $9_1$, $9_2$, $9_3$, 18A, 23A are closed.

Via the pipe 15A, a predetermined volume of standard is fed into the circuit 1A such that the standard partially fills the mixing chamber 20A. After opening of the valves $9_1$, $9_2$, $9_3$, the necessary quantities of reactants are introduced into the circuit 1A and consequently into the mixing chamber 20A. The valves $9_1$, $9_2$, $9_3$ are then closed again. The reactants and the standard mix in the mixing chamber 20A.

The microwave generator is run and the reaction chamber 2A in the microwave application cavity 3A is thereby heated.

The valve 23A is opened and the mixture comprising the standard and the reactants flows from the mixing chamber 20A to the reaction chamber 2A. On passing into the reaction chamber 2A, the mixture is heated for a predetermined time which is a function of the geometrical features of the reaction chamber 2A. The chemical reaction takes place, and the product of the reaction related to the standard flows out via the outflow pipe 7A.

When all the product of the reaction has been recovered, the valve 10A of the rinsing liquid feed pipe 6A is opened and the circuit 1A is rinsed. The apparatus is thus calibrated and ready for carrying out a chemical reaction by the wet method on a succession of samples.

Accordingly, then, with the valves 10A, $9_1$, $9_3$, 18A, 23A, 25A closed, the valve 8A of the sample feed pipe 4A is opened, and the receptacle 16A is filled to a level above the overflow outlet 17A; the valve 8A is then closed.

The valve 18A is opened and the excess sample flows out via the overflow 17A; the sample volume present in the receptacle 16A and which will be fed into the circuit 1A is hence perfectly defined.

The valve 25A is opened and the sample flows into the mixing chamber 20A. The valve $9_1$, $9_2$, $9_3$ are opened and the necessary reactants are introduced into the circuit 1A and consequently into the mixing chamber 20A.

The microwave generator is run and the reaction chamber 2A in the microwave application cavity 3A is heated.

The valve 23A is opened and the mixture comprising the sample and the reactants flows form the mixing chamber 20A to the reaction chamber 2A, where it is heated for a predetermined time. The chemical reaction takes place, and the product of the reaction of the sample flows out via the outflow pipe 7A.

When all the product of the reaction has been recovered, the valve 10A of the rinsing liquid feed pipe 6A is opened and the circuit 1A is rinsed.

The apparatus is then ready for carrying out a chemical reaction by the wet method on another sample, after opening of the valve 8A of the sample feed pipe 4A.

The above-described operations leading to the chemical reaction on the sample will be repeated as many times as necessary until the succession of samples is exhausted.

The apparatus for carrying out a chemical reaction on a succession of samples according to the embodiment shown in FIG. 3 contains a circuit which is a looped circuit 100B.

In the present text, reference has been made, when considering the direction of travel of the sample in the circuit, to upstream and downstream locations with respect to the reaction chamber in order to situate the various components constituting the circuit.

In the looped circuit, any product, such as sample, standard, reactant or rinsing liquid, which is to pass through the reaction chamber is fed or introduced upstream of the latter via pipes opening into the circuit upstream of the reaction chamber. Thus, the product of the reaction is recovered downstream of the reaction chamber since it no longer passes through the latter, and the outflow pipe of the product of the reaction is hence situated downstream of the reaction chamber.

The looped circuit 100B of the apparatus for chemical reaction according to the invention comprises: a reaction chamber 2B placed in the microwave application cavity 3B of a wave guide 13B, a cooling zone 26B placed at the point of outflow of the reaction chamber 2B, means 14B for adjustment of the volume of the sample, and circulation means 27B.

The cooling zone 26B can comprise a coil 28B passing through a cooling mixture.

The means of adjustment 14B of the volume of the sample comprises, according to the present embodiment, an expansion vessel which is in the form of a graduated receptacle 29B equipped with a drainage pipe 30B carrying a valve 31B. The means of adjustment 14B of the sample volume are, of course, placed upstream of the reaction chamber 2B. The pipe for linkage 33B of the receptacle 29B to the remainder of the looped circuit 100B is provided with a valve 34B.

The receptacle 29B is open at the top in order to enable the gases evolved in the chemical reaction to escape.

The receptacle 39B of the means of adjustment 14B of the sample volume constitutes the expansion vessel of the looped circuit 100B.

The circulation means 27B can comprise a positive-displacement pump delivering a continuous flow; an embodiment of such a pump will be described later.

Connection means (not shown) are associated with the pump 27B, enabling:

the sample fed via the pipe 4B to be drawn-in and delivered to the receptacle 29B, via conduit 33B, the sample, and then the sample mixed with the reactants present in the receptacle 29B, to be drawn-in and delivered to the reaction chamber 2B, the rinsing liquid fed via the pipe 6B to be drawn-in and delivered to the reaction chamber 2B.

Upstream of the reaction chamber 2B, the circuit 100B comprises:

a sample feed pipe 4B equipped with a valve 8B and linked to a sampling line, a rinsing liquid feed pipe 6B equipped with a valve 10B, these two pipes 4B, 6B being linked to the suction inlet of the pump 27B, pipes $5_1$, $5_2$, $5_3$ for introduction of the reactants, each carrying a positive-displacement injection pump $32_1$, $32_2$, $32_3$ and a valve $9_1$, $9_2$, $9_3$.

In addition, a pipe 39B for conveying compressed gas, equipped with a valve 42B, opens into the looped circuit 100B directly at the point of entry of the reaction chamber 2B.

Downstream of the reaction chamber 2B, the circuit 100B comprises an outflow pipe 7B for the product of the reaction, equipped with a valve 11B, which pipe is, according to the present embodiment, combined with the graduated receptacle 29B.

The carrying out of a chemical reaction by the wet method on a succession of samples by means of the apparatus according to the embodiments shown in FIG. 3 will be described below.

With the sample feed pipe 4B and the rinsing liquid feed pipe 6B linked, respectively, to a source of samples and to a source of rinsing liquid, and all the valves in the circuit 100B closed beforehand, the pump 27B is started. The valve 34B and the valve 8B of the sample feed pipe 4B are opened, and the graduated receptacle 29B of the means of adjustment 14B of the sample volume is filed via conduit 33. The valves 8B and 34B are closed, and the valve 31B of the drainage pipe 30B is then opened; when the level of the sample reaches the graduation of the receptacle 29B corresponding to the chosen volume, the valve 31B is closed. The sample volume present in the receptacle and which will be fed into the circuit 100B is hence perfectly defined.

The valve 34B is opened and the predetermined quantity of sample is fed into the looped circuit 100B, the sample being circulated in the looped circuit 100B by means of the pump 27.

The pump $32_1$ for injection of a first reactant, conveyed via the pipe $5_1$, is started and the valve $9_1$ is opened; a first reactant is thereby introduced into the looped circuit 100B. The valve $9_1$ is then closed again and the pump $32_1$ is stopped.

The mixture composed of the sample and the first reactant is transferred to the receptacle 29B and then flows into the reaction chamber 2B where it is heated, the microwave generator having been set running beforehand.

The product of the first reaction of the sample and the first reactant is then cooled by passage through the coil 28B of the cooling zone 26B.

The product of the first reaction continue to flow in the circuit 100B when the pump $32_2$ for injection of a second reactant, conveyed via the pipe $5_2$, is started. The valve $9_2$ is then closed again, and the pump $32_2$ is stopped.

The mixture composed of the product of the first reaction and the second reactant is transferred to the receptacle 29B and then flows into the reaction chamber 2B where it is heated, the mixture thus undergoing the second reaction.

The product of the second reaction is then cooled by passage through the coil 28B of the cooling zone 26B.

The same operations are repeated for the third reactant.

Then, the valve 34B is closed and the pump 27B is stopped; the valve 42B of the pipe 39B for conveying compressed gas is then opened. The valve 11B of the outflow pipe 7B for the product of the reaction is opened, and the gas drives the product of the reaction round the looped circuit 100B, the product being recovered.

When all of the product of the reaction has been recovered, the valve 42B and the valve 11B of the outflow pipe 7B are closed again° The valve 34B and the valve 10B of the rinsing liquid feed pipe 6B are opened. The pump 27B is started, and the circuit is rinsed by circulating the liquid in the looped circuit 100B. The valve 11B of the outflow pipe 7B is opened and the contaminated rinsing liquid is directed to an effluent storage tank; the valve 10B of the rinsing liquid feed pipe 6B and the valve 11B of the outflow pipe 7B are then closed.

The apparatus is then ready for carrying out a chemical reaction by the wet method on another sample.

The apparatus for carrying out a chemical reaction on a succession of samples according to the embodiment shown in FIG. 4 contains a circuit which is a looped circuit 100C. This looped circuit 100C is similar to the looped circuit according to the embodiment shown in FIG. 3, and only the constituent components which are different will be described.

According to the present embodiment, the means of adjustment 14C of the volume of the sample comprises a receptacle 16C equipped with an overflow outlet 17C carrying a valve 18C. The receptacle 16C is not open to the air; it is provided with a leakproof lid 35C equipped with a vent 36C carrying a valve 37C. Such a receptacle makes it possible to be able to carry out chemical reactions at atmospheric pressure or under pressure by closing the valve 37C.

The vent 36C can optionally be linked to a vapor condenser or to a device for recovering gases evolved in the chemical reaction.

The looped circuit 100C contains three pipes $5_1$, $5_2$, $5_3$ for introduction of reactants mounted in parallel and linked to a common pipe 38C in which a positive-displacement pump 32C for injection of the reactants is placed. Each pipe $5_1$, $5_2$, $5_3$ carries a valve $9_1$, $9_2$, $9_3$.

The looped circuit 100C also contains a standard feed pipe 15C carrying a valve 40C.

The apparatus according to the embodiment shown in FIG. 4 contains, in addition, means 41C for monitoring the progress of the reaction, for example by colorimetry.

The carrying out of a chemical reaction by the wet method on a succession of samples by means of the apparatus according to the present embodiment will be described below.

With the sample feed pipe 4C and the rinsing liquid feed pipe 6C linked, respectively, to a source of samples and to a source of rinsing liquid, and all the valves in the circuit 100C closed beforehand, the pump 27C is started. The valve 34C and the valve 40C of the pipe 15C for feeding the standard are opened and the receptacle 16C of the means of adjustment 14C of the sample volume is filled to a level about the overflow outlet 17C; the valve 40C is then closed. The valve 18C is then opened and the excess standard flows out via the overflow 17C; the volume of standard present in the receptacle 16C and which will be fed into the looped circuit 100C is hence perfectly defined. The valve 18C is closed again.

The valve 34C is opened and the predetermined quantity of standard is fed into the looped circuit 100C. The standard is circulated in the looped circuit 100C by means of the pump 27C.

The pump 32C for injection of reactant is started and the valve $9_1$, of the pipe $5_1$ for introduction of the first reactant is opened; a first reactant is thereby introduced into the looped circuit 100C. The valve $9_1$ is then closed again and the pump 32C is stopped.

The mixture composed of the standard and the first reactant is transferred to the receptacle 16C and then flows into the reaction chamber 2C where it is heated, the microwave generator having been set running beforehand.

The product of the first reaction of the standard and the first reactant is then cooled by passage through the coil 28C of the cooling zone 26C.

The product of the first reaction continues to flow in the circuit 100C; the pump 32C for injection of a second reactant, conveyed via the pipe $5_2$, is started and the valve $9_2$ is opened. A second reactant is thereby introduced into the looped circuit 100C. The valve $9_2$ is then closed again and the pump 32C is stopped.

The mixture composed of the product of the first reaction and the second reactant is transferred to the receptacle 16C and then flows into the reaction chamber 2C where it is heated, the mixture undergoing the second reaction.

The product of the second reaction is then cooled by passage through the coil 28C of the cooling zone 26C.

Then the third reactant is introduced and heated within the reaction chamber along with the product of the second reaction.

The valve 34C is closed and the valve 7C of the outflow pipe 11C and the valve 10C of the rinsing liquid feed pipe 6C are opened.

The rinsing liquid, under the effect of the pump 27C, flows in the looped circuit 100C and drives before it the product of the reaction, which is recovered via the pipe 7C. When all the product of the reaction has been recovered, the contaminated rinsing liquid is directed to an effluent storage tank. The looped circuit 100C is hence rinsed.

The apparatus is then ready for carrying out a chemical reaction by the wet method on samples, repeating the above operations on each sample of the succession.

Naturally, after each injection of reactant and each reaction, the progress of the chemical reaction is monitored by the monitoring means 41C. The period of heating of the product in the reaction chamber 2C may be increased or decreased by varying the output of the pump 27C.

It is also possible to increase the period of heating of the product in the reaction chamber 2C by establishing a recirculation of the product in the looped circuit 100C after each injection of reactant. In this case, the looped circuit 100C advantageously contains a shunt 43C which can be isolated by three-way valves 44C, 45C, thereby enabling cooling of the product of the reaction by passage through the coil 28C of the cooling means 26C to be avoided.

Figure 5A:
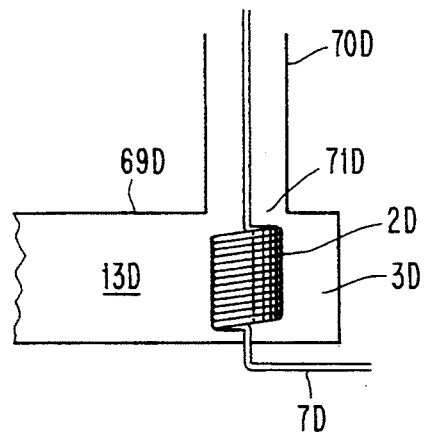
FIGS. 5a, 5b, and 5c show three different methods of providing a reaction chamber in a microwave application cavity according to the invention.
Figure 5B:
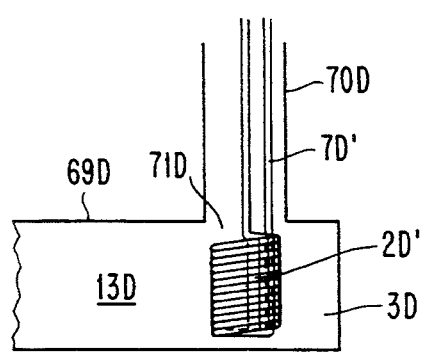
Figure 5C:
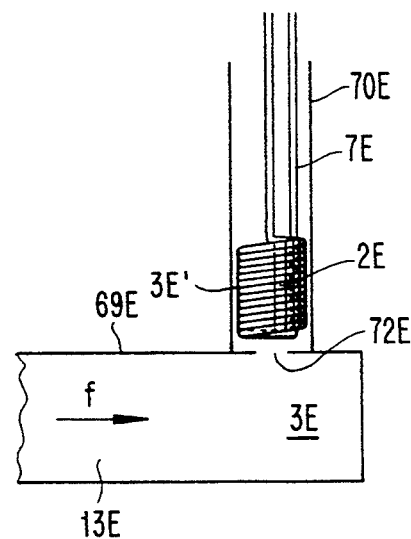

FIGS. 5a, 5b and 5c show diagrammatically three different ways of setting-up the reaction chamber in a microwave application cavity.

According to FIGS. 5a and 5b, the microwave application cavity 3D is, more specifically, the microwave application cavity of a MICRODIGEST 300, an apparatus marketed by the company PROLABO.

In this apparatus, the application cavity 3D has in its upper wall 69D an opening 71D which enables the reaction chamber 2D (or 2D') to be placed in the microwave application cavity 3D. The application cavity 3D possesses a duct 70D surrounding the opening 71D and rising to a height such that it forms a microwave absorption barrier. In FIG. 5a the outflow pipe 7D extends downwardly through a floor of the wave guide 13D, whereas in FIG. 5b the outflow pipe 7D' extends upwardly through the duct 70D.

According to FIG. 5c, the microwave application cavity 3E is, more specifically, the microwave application cavity of a MAXIDIGEST MX 350, an apparatus marketed by the company PROLABO.

In this apparatus, the wave guide 13E contains an opening 72E provided in its upper wall 69E. This opening constitutes a coupling window inclined with respect to the direction of propagation f of the microwaves in the application cavity 3E. The coupling window 72E provides for a propagation of the microwaves inside the duct 70, which constitutes a secondary application cavity 3E' in which the reaction chamber 2E is placed.

Figure 6:
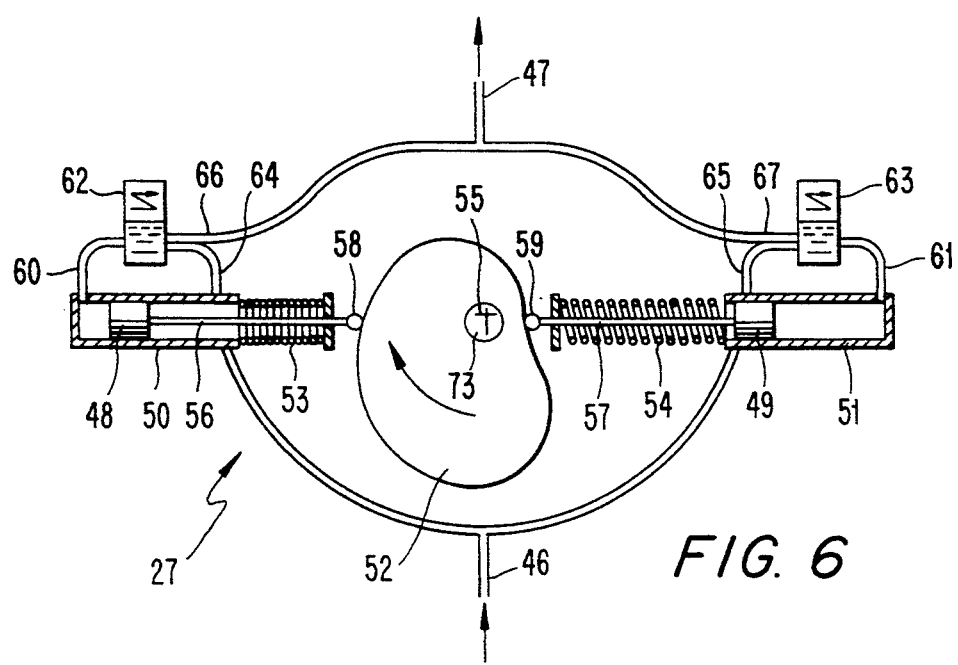
FIG. 6 is a schematic cross-sectional view of a preferred circulation pump according to the invention.

The circulation means, according to the embodiment shown in FIG. 6, are advantageously used in the apparatus for carrying out a chemical reaction by the wet method on a succession of samples, which is the subject of the invention. These circulation means are composed of a pump 27 which corresponds to the previously discussed pump 27, 27C. The pump 27 is linked to two pipes 46, 47 for connection of the pump 27 within a circuit.

The pump 27 contains two plungers 48, 49 mounted in opposition, traveling in two barrels 50, 51. An alternating linear motion is imparted to the plungers by means of a flat cam 52, possessing a suitable profile. The plungers are biased toward the cam by return means comprising two springs 53, 54. The plungers 48, 49 are mounted symmetrically with respect to the axis of rotation 55 of the cam 52.

The rod 56, 57 of each plunger 48, 49 is guided linearly and is equipped with an anti-rotation device. The rods 56, 57 of the plungers 48, 49 bear on the cam 52 via rollers 58, 59. Permanent contact between the rollers 58, 59 and the cam 52 is effected by the springs 53, 54.

The axle 73 of the cam 52 is driven in rotation; it is oriented perpendicularly to the axis of travel of the plungers 48, 49. The axle 73 may be driven by means of a motor and a transmission, for example by a belt or by gearwheels. Preferably, in order to avoid play or slipping, the cam 52 is directly mounted on the final drive shaft of a geared motor rotting at a slow, constant and accurately known speed.

Each barrel 50, 51 has its outflow 60, 61 linked to a three-way, two-position electromagnetic valve 62, 63. Two inflows 64 and 65 of the electromagnetic valves 62, 63 are linked to one another and to the pipe 46, and two outflows 66 and 67 are linked to one another and to the pipe 47.

The operation of the electromagnetic valves 62, 63 is controlled by means of electrical contacts activated at very precise angular positions of the cam 52. Thus, when each plunger is being retracted by its respective spring 53 or 54, the associated valve 62 or 63 is operated to enable fluid from the respective inflow 64 or 65 to enter the barrel 50 or 51. Then, when the cam extends the plunger against the spring bias, the valve is shifted to enable the fluid to be expelled through the associated outflow 66 or 67. It will be appreciated that the plungers operate 180° out-of-phase, i.e., one plunger is being retracted while the other is being extended.

The motion of the two plungers 48, 49 is determined by the shape of the cam 52. The profile of the latter is defined in such a way that the instantaneous sum of the speeds of advance of the plungers is constant.

The output obtained with such circulation means is perfectly regular, even at very low outputs, and is independent of the delivery pressure. Such circulation means are also positive in their displacement, one rotation of the cam delivering two barrel volumes. By knowing the speed of rotation of the cam, it is an easy matter to work out accurately the flow rate of liquid flowing in the circuit, and especially in the reaction chamber.

Naturally, the invention in no way limited to the embodiments described specifically in the present description, and variants or improvements relating to the various means employed may be adopted without thereby departing from the scope of the invention.

Without departing from the scope of the invention, it is also possible to combine with one another two or more constituent components of the apparatus which have been described above only by way of examples and are in no way limiting.

The apparatus and the process for chemical reaction by the wet method on a succession of samples are intended for carrying out a wide variety of chemical reactions. They are intended especially for carrying out chemical reactions such as the acid or alkaline treatment of samples by the wet method for purposes of dissolution, hydrolysis or mineralization.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for carrying out a chemical reaction by a wet method on a succession of samples, said apparatus comprising:
   a looped circuit;
   a microwave chamber;
   a reaction chamber positioned in said microwave chamber and communicating with said circuit;
   a sample feed pipe communicating with said circuit upstream of said reaction chamber and connected to a source of samples;
   a reactant feed pipe communicating with said circuit upstream of said reaction chamber and connected to a source of reactants;
   a rinsing liquid feed pipe communicative with said circuit upstream of said reaction chamber and connected to a source of rinsing liquid;
   valves disposed respectively in said sample feed pipe, said reactant feed pipe, and said rinsing liquid feed pipe;
   an outflow pipe communicating with said reaction chamber for conducting a product of a reaction occurring in said reaction chamber;
   circulation means for inducting a forced circulation through said circuit, said circulation means comprising a pump including first and second barrels each having an inlet and an outlet communicating with said circuit, valve means operably connected to said first and second barrels for alternately connecting each barrel to its inlet and outlet, first and second plungers each having a plunging end and a driven end, each plunging end disposed for reciprocation in a respective barrel for performing retraction and extension strokes while said respective barrel is connected to its inlet and outlet, respectively, a rotationally driven cam having an endless cam surface means, said driven ends of said first and second plungers being arranged to slidably engage said cam surface means at locations thereon for being reciprocated 180 degrees out of phase;
   cooling means for cooling the product of reaction, said cooling means including an inlet and an outlet, said inlet communicating with said outflow pipe for receiving the product of reaction to be cooled;
   a shunt disposed outside of said cooling means and communicating with said inlet and outlet of said cooling means by valves actuable for enabling the product of reaction to bypass said cooling means;
   monitoring means connected to said outlet of said cooling means for monitoring the progress of the reaction; and
   an expansion vessel disposed downstream of said monitoring means for receiving the product of reaction and supplying same to said reaction vessel, said expansion vessel including a leakproof lid and a valved vent.

2. Apparatus according to claim 1 including a standard feed pipe communicating with said circuit upstream of said reaction chamber and connected to a source of standard.

3. Apparatus according to claim 1 including a valve in said circuit located downstream of said reaction chamber for closing said circuit while the reaction occurs in said reaction chamber.

4. Apparatus according to claim 1 including first and second spring means for biasing said driven ends of said first and second plungers, respectively, against said cam surface means.

* * * * *